(12) United States Patent
Chen et al.

(10) Patent No.: US 11,554,355 B2
(45) Date of Patent: Jan. 17, 2023

(54) MICRO REACTION SYSTEM AND METHOD FOR PREPARING 2-METHYL-4-AMINO-5-CYANOPYRIMIDINE USING SAME

(71) Applicant: Fudan University, Shanghai (CN)

(72) Inventors: Fener Chen, Shanghai (CN); Meifen Jiang, Shanghai (CN); Dang Cheng, Shanghai (CN); Minjie Liu, Shanghai (CN); Huashan Huang, Shanghai (CN)

(73) Assignee: Fudan University, Shanghai (CN)

( * ) Notice: Subject to any disclaimer, the term of this patent is extended or adjusted under 35 U.S.C. 154(b) by 0 days.

(21) Appl. No.: 17/467,060

(22) Filed: Sep. 3, 2021

(65) Prior Publication Data

US 2021/0394149 A1  Dec. 23, 2021

(30) Foreign Application Priority Data

Nov. 5, 2020  (CN) .......................... 202011222230.4

(51) Int. Cl.
*B01J 19/00* (2006.01)
*C07D 239/42* (2006.01)

(52) U.S. Cl.
CPC ........ *B01J 19/0093* (2013.01); *C07D 239/42* (2013.01); *B01J 2219/00889* (2013.01);
(Continued)

(58) Field of Classification Search
CPC ......... B01J 8/00; B01J 8/02; B01J 8/06; B01J 8/065; B01J 19/00; B01J 19/0093; B01J 23/00; B01J 23/70; B01J 23/74; B01J 23/755; B01J 25/00; B01J 25/02; B01J 2219/00; B01J 2219/00781; B01J 2219/00889; B01J 2219/00905; B01J 2219/00909; B01J 2219/0095; B01J 2219/00952; B01J 2219/00954;
(Continued)

(56) References Cited

U.S. PATENT DOCUMENTS 2,184,720 A  12/1939  Matukawa et al.
2,235,638 A  3/1941   Hromatka
(Continued)

FOREIGN PATENT DOCUMENTS

CH  193951 A  11/1937
CH  193952 A  11/1937
(Continued)

OTHER PUBLICATIONS

Machine translation of DE 1135913 B, which was published on Mar. 1, 1962. (Year: 1962).*

(Continued)

*Primary Examiner* — Natasha E Young

(57) ABSTRACT

Disclosed herein relates to pharmaceutical engineering, and more particularly to a micro reaction system and a method for preparing 2-methyl-4-amino-5-cyanopyrimidine using the same. An acetamidine hydrochloride solution and an (dimethylaminomethylene)malononitrile solution are separately pumped into the micro reaction system including a micromixer and an agitating microchannel reactor in communication at the same time for a continuous condensation-cyclization reaction to obtain 2-methyl-4-amino-5-cyanopyrimidine.

11 Claims, 1 Drawing Sheet

(52) U.S. Cl.
CPC ............... *B01J 2219/00909* (2013.01); *B01J 2219/00961* (2013.01); *B01J 2219/00963* (2013.01)

(58) Field of Classification Search
CPC .... B01J 2219/00959; B01J 2219/00961; B01J 2219/00963; B01J 2219/00984; C07D 239/00; C07D 239/02; C07D 239/24; C07D 239/28; C07D 239/32; C07D 239/42
See application file for complete search history.

(56) References Cited

U.S. PATENT DOCUMENTS

| | | | |
|---|---|---|---|
| 2,271,503 A | | 1/1942 | Wuest et al. |
| 3,655,716 A | | 4/1972 | Leimgruber et al. |
| 3,689,498 A | | 9/1972 | Leimgruber et al. |
| 3,742,015 A | | 6/1973 | Leimgruber et al. |
| 3,792,076 A | | 2/1974 | Leimgruber et al. |
| 3,853,946 A | | 12/1974 | Leimgruber et al. |
| 3,900,511 A | | 8/1975 | Leimgruber et al. |
| 3,901,888 A | | 8/1975 | Leimgruber et al. |
| 3,965,141 A | | 6/1976 | Leimgruber et al. |
| 3,966,791 A | | 6/1976 | Leimgruber et al. |
| 2006/0292062 A1* | 12/2006 | Hojo ..................... C01G 19/02 423/594.9 |
| 2016/0145249 A1* | 5/2016 | Terakado ................ A61P 11/00 546/209 |

FOREIGN PATENT DOCUMENTS

| | | | | |
|---|---|---|---|---|
| CN | 103261173 A | | 8/2013 | |
| DE | 667990 C | | 11/1938 | |
| DE | 670635 C | | 1/1939 | |
| DE | 671787 C | | 2/1939 | |
| DE | 113591 B | * | 3/1962 | ........... C07D 239/42 |
| DE | 3641604 A1 | | 6/1988 | |
| EP | 0055108 B1 | | 9/1984 | |
| FR | 819596 A | | 10/1937 | |
| WO | 2012075677 A1 | | 6/2012 | |

OTHER PUBLICATIONS

Grewe R .Über das antineuritische Vitamin. 5. Mitteilung. physiol. Chem. 242 , 89 (1936).

Grewe R . Die Konstitution des Aneurins (Vitamin B1 )[J]. Naturwissenschaften, 1936, 24(42):657.

Todd artd Bergel.a method for preparing 2-methyl-4-amino-5-aminomethyl pyrimidine through hydrolysis of 2-methyl-4-amino-5-acetamidomethyl pyrimidine.(J. Chem. Soc., 1937, 364).

Fener Chen et al. 2-methyl-4-amino-5-cyanopyrimidine was catalytically hydrogenated to prepare 2-methyl-4-amino-5-aminomethyl pyrimidine.(Org. Process. Res. Dev., 2012, 16, 57).

* cited by examiner

MICRO REACTION SYSTEM AND METHOD FOR PREPARING 2-METHYL-4-AMINO-5-CYANOPYRIMIDINE USING SAME

CROSS-REFERENCE TO RELATED APPLICATIONS

This application claims the benefit of priority from Chinese Patent Application No. 202011222230.4, filed on Nov. 5, 2020. The content of the aforementioned application, including any intervening amendments thereto, is incorporated herein by reference in its entirety.

TECHNICAL FIELD

This disclosure relates to pharmaceutical engineering, and more particularly to a micro reaction system and a method for preparing 2-methyl-4-amino-5-cyanopyrimidine using the same.

BACKGROUND 2-methyl-4-amino-5-cyanopyrimidine has a structure of formula (I):

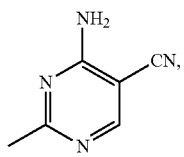

(I)

and is a key intermediate in the synthesis of vitamin Bi. German patent No. 671787, French patent No. 819596, Norwegian patent No. 59015 and Swiss patent Nos. 193951 and 193952 all disclosed a method for synthesizing the compound (I), in which malonate was used as a starting material, and reacted with triethyl orthoformate to prepare ethoxymethylene malonate. The ethoxymethylene malonate was condensed with acetamidine hydrochloride to synthesize 2-methyl-4-hydroxy-5-alkoxycarbonylpyrimidine, which was subjected to chlorination, amidation and dehydration to prepare the compound (I). This method had multiple synthesis steps and a low yield of final product due to a relatively poor condensation efficiency (60%), and thus it was greatly limited in the industrial application. Todd and Bergel (*J. Chem. Soc.*, 1937, 364) used cyanoacetate as a starting material to react with triethyl orthoformate to prepare ethoxymethylene cyanoacetate, which was condensed with acetamidine hydrochloride, and subjected to amidation and dehydration to obtain the compound (I). By comparison, the latter had a shortened process route, but struggled with a poor yield (32%) of the condensation of ethoxymethylene cyanoacetate and acetamidine hydrochloride.

As disclosed by U.S. Pat. Nos. 3,655,716, 3,742,015, 3,900,511, 3,965,141 and 3,966,791, 3-(dimethylamino)propionitrile or N,N-dimethylformamide diethyl acetal, as a starting material, was converted into an intermediate 3-(dimethylamino) acrylonitrile, which was then subjected to a Vilsmeier reaction with dimethylformamide/phosphorus oxychloride to synthesize 3-dimethylamino-2-cyano-acrolein. Finally, the 3-dimethylamino-2-cyano-acroleine was reacted with O-acetylhydroxylamine hydrochloride to obtain (dimethylaminomethylene)malononitrile, which subsequently underwent amination and cyclization to obtain the compound (I). This strategy had a long synthetic route, complicated process, high cost and serious environmental pollution, and thus it was also not practicable for industrial production. In U.S. Pat. Nos. 3,689,498, 3,792,076, 3,853, 946 and 3,901,888, 3-dimethylamino-2-cyano-acrolein was synthesized using the above-mentioned method, and then reacted with hydroxylamine hydrochloride to synthesize 3-dimethylamino-2-cyanoacrylamide, which was then condensed with acetamidine hydrochloride and dehydrated to obtain the compound (I). Unfortunately, this method was limited by harsh reaction conditions during the preparation of 3-(dimethylamine)acrylonitrile, high requirements for the equipment and high cost of N,N-dimethylformamide diethyl acetal.

It has been published in some patent literatures (German patent No. 3641604 and European patent No. 55108) that acetonitrile, as a starting material, was reacted with ethyl formate/sodium methoxide to prepare sodium 3-hydroxyacrylonitrile, and the sodium 3-hydroxyacrylonitrile experienced formylation and alcoholysis to synthesize 3-dimethoxypropionitrile, which was subjected to formylation, cyclization and oximation to obtain the compound (I). Japanese patent No. 58128356 disclosed a method for preparing the compound (I) by subjecting sodium 3-hydroxyacrylonitrile to formylation, methylation, cyclization and oximation subsequently. Nishihira and Nakai (*Kagaku Kogaku*, 1991, 55, 433) and Yoshida et al. (*Nikkakyo Geppo*, 1992, 45, 6) reported a synthetic route, in which acrylonitrile was used as a starting material, and reacted with nitromethane to synthesize 3-dimethoxypropionitrile, which was subjected to formylation, butylation, cyclization and oximation to obtain the compound (I). These methods all had long synthetic routes, complicated process and high cost.

Grewe et al. (*Physiol. Chem.*, 1936, 242, 89; *Naturwiss*, 1936, 24, 657) reported that malononitrile and triethyl orthoformate were condensed to synthesize ethoxymethylene malononitrile, which was then condensed with acetamidine hydrochloride to obtain the compound (I). Though this method had shortened synthetic route, the yield of the condensation of ethoxymethylene malonate and acetamidine hydrochloride was still unsatisfactory.

Similarly, U.S. Pat. Nos. 2,235,638, 2,271,503, and 2,184, 720, German patent Nos. 667990 and 670635 and Japanese patent No. 55505070 also adopted malononitrile as a starting material to condense with triethyl orthoformate to prepare ethoxymethylene malonate, which was then subjected to ammonolysis with ammonia gas to produce (dimethylaminomethylene)malononitrile. The (dimethylaminomethylene) malononitrile is then cyclized with iminoethoxyethane hydrochloride to obtain the compound (I). Though the method had a short synthetic route, the final cyclization required 1.8 equivalents of iminoethoxyethane hydrochloride with high price, increasing the total cost.

As suggested by world patent No. 2012/075677, Chinese patent No. 103261173 and Fener Chen et al. (*Org. Process. Res. Dev.*, 2012, 16, 57), a cheap chemical cyanoacetamide was also suitable as a starting material for the preparation of the compound (I). Specifically, cyanoacetamide was dehydrated in situ to produce malononitrile, and the malononitrile was reacted with a Vilsmeier reagent to obtain (dimethylaminomethylene)malononitrile, which was then condensed with acetamidine hydrochloride to obtain the compound (I). This method had reduced cost and simplified process route, however, it still struggled with complicated operation of the condensation between (dimethylaminomethylene)malononitrile and acetamidine hydrochloride, a low yield (only about 60%), time-consuming reaction (15-20 h) and high energy consumption.

These methods are all carried out in traditional batch reactors. In view of this, there is an urgent need for those skilled in the art to develop a rapid, simple, economical, low-energy consumption and efficient method for continuously preparing 2-methyl-4-amino-5-cyanopyrimidine (I) with high yield to overcome the defects in the existing methods.

SUMMARY

An object of this disclosure is to provide a method for preparing 2-methyl-4-amino-5-cyanopyrimidine using a micro reaction system to overcome the drawbacks of the prior art. The method provided herein has shortened reaction time, improved efficiency and yield of 2-methyl-4-amino-5-cyanopyrimidine, simplified operation, enhanced automation and reduced energy consumption and cost, and thus it is promising in the industrial application.

Technical solutions of this disclosure are described as follows.

In a first aspect, this disclosure provides a method for preparing 2-methyl-4-amino-5-cyanopyrimidine using a micro reaction system, wherein the micro reaction system comprises a micromixer and an agitating microchannel reactor communicated in sequence, and the method comprises:

(1) pumping an acetamidine hydrochloride solution and a (dimethylaminomethylene)malononitrile solution separately into the micromixer at the same time followed by mixing;

(2) allowing the reaction mixture flowing out of the micromixer to enter the agitating microchannel reactor; and subjecting the reaction mixture to condensation-cyclization reaction; and (3) collecting the reaction mixture flowing out of the micro reaction system; and subjecting the reaction mixture to separation and purification to obtain a target product 2-methyl-4-amino-5-cyanopyrimidine;

wherein the 2-methyl-4-amino-5-cyanopyrimidine is shown in formula (I); the acetamidine hydrochloride is shown in formula (II); the (dimethylaminomethylene)malononitrile is shown in formula (III); the condensation-cyclization reaction is shown in the following reaction scheme:

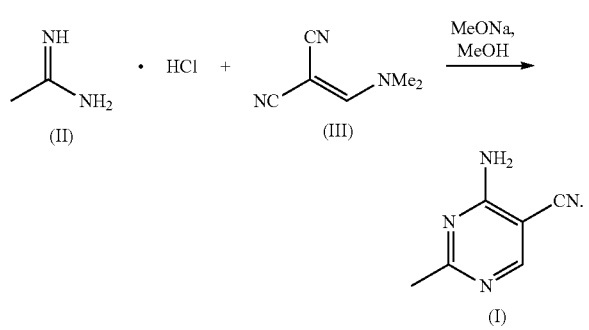

In some embodiments, in step (1), the acetamidine hydrochloride solution is prepared by dissolving acetamidine hydrochloride in a methanol solution containing sodium methoxide at −20-15° C.; a molar concentration of sodium methoxide in the methanol solution is 0.5-7 mol/L; and a molar ratio of acetamidine hydrochloride in the acetamidine hydrochloride solution to the sodium methoxide is 1:0.7-1.3.

In some embodiments, in step (1), the (dimethylaminomethylene)malononitrile solution is prepared by dissolving (dimethylaminomethylene)malononitrile in methanol; and a molar concentration of the (dimethylaminomethylene)malononitrile in the (dimethylaminomethylene)malononitrile solution is 0.8-1.8 mol/L.

In some embodiments, in step (1), the micromixer is a static mixer, a T-shaped micromixer, a Y-shaped micromixer, a coaxial flow micromixer or a flow-focusing micromixer.

In some embodiments, in step (1), flow rates of the acetamidine hydrochloride solution and the (dimethylaminomethylene)malononitrile solution pumped into the micromixer are controlled to adjust a molar ratio of the acetamidine hydrochloride to the (dimethylaminomethylene)malononitrile to 1:0.6-1.2.

In some embodiments, in step (1), a temperature in the micromixer is controlled at −10-100° C.

In some embodiments, in step (2), the agitating microchannel reactor comprises:
at least one reaction plate; and
at least one heat exchange plate;
wherein the at least one heat exchange plate fastened to the at least one reaction plate; each of the at least one reaction plate is provided with at least one inlet channel, at least one outlet channel, N reaction fluid channel(s) and N+1 mixing chambers, wherein N is an integer equal to or greater than 1; each of the N+1 mixing chambers is a three-dimensional cavity; each of the N+1 mixing chambers is provided with a stirrer therein; the N+1 mixing chambers are communicated with the N reaction fluid channel(s); one end of the at least one inlet channel is connected to an inlet of the agitating microchannel reactor, and the other end of the at least one inlet channel is communicated with a mixing chamber adjacent thereto; one end of the at least one outlet channel is connected to an outlet of the agitating microchannel reactor, the other end of the at least one outlet channel is communicated with a mixing chamber adjacent thereto; each of the at least one heat exchange plate is provided with a temperature-control medium channel; two ends of the temperature-control medium channel are provided with a temperature-control medium inlet and a temperature-control medium outlet; and the agitating microchannel reactor is arranged at a base or a support that is vibratile horizontally or vertically with a constant amplitude.

In some embodiments, a hydraulic diameter of the at least one inlet channel is 0.1-20 mm.

In some embodiments, a hydraulic diameter of the at least one outlet channel is 0.1-20 mm.

In some embodiments, a hydraulic diameter of the N reaction fluid channel(s) is 0.1-20 mm.

In some embodiments, a depth of each of the N+1 mixing chambers is 40-90% of a thickness of the at least one reaction plate.

In some embodiments, a hydraulic diameter of a cross-section of each of the N+1 mixing chambers is 2-50 mm.

In some embodiments, a volume of each of the N+1 mixing chambers is 1-50 mL.

In some embodiments, the stirrer is 30-95% by volume of each of N+1 the mixing chambers.

In some embodiments, a vibration frequency of the base or support is controlled at 0-15 Hz.

In some embodiments, the N+1 mixing chambers are cylindrical or prismatic.

In some embodiments, each of the N+1 mixing chambers is connected to the at least one inlet or outlet channel.

In some embodiments, the agitating microchannel reactor is a Coflore agitated cell reactor (AM Technology Co., Ltd, UK).

In some embodiments, in step (2), a temperature in the agitating microchannel reactor is controlled at 0-100° C.

In some embodiments, in step (2), a residence time of the reaction mixture in the agitating microchannel reactor is controlled to 1-60 min.

In some embodiments, the micro reaction system further comprises:
a first pump for feeding the acetamidine hydrochloride solution;
a second pump for feeding the (dimethylaminomethylene)malononitrile solution;
a gas-liquid separator; and
a back pressure valve;
wherein a first inlet of the micromixer is connected to the first pump; a second inlet of the micromixer is connected to the second pump; an outlet of the micromixer is connected to an inlet of the agitating microchannel reactor; a top of the gas-liquid separator is provided with a first port, a second port and a third port; the first port is connected to an outlet of the agitating microchannel reactor; the second port is configured to introduce nitrogen to provide a pressure in the gas-liquid separator, where a pressure of the nitrogen is 0-2.5 MPa; the third port is connected to the back pressure valve, where a back pressure of the back pressure valve is 0-2 MPa; and the pressure of the nitrogen is 0-0.5 MPa larger than a back pressure set by the back pressure valve.

In some embodiments, the step (3) specifically comprises:
collecting the reaction mixture flowing out of the micro reaction system; filtering the reaction mixture to collect a filter residue; and washing and drying the filter residue to obtain a target product 2-methyl-4-amino-5-cyanopyrimidine.

In a second aspect, this disclosure provides a micro reaction system for preparing 2-methyl-4-amino-5-cyanopyrimidine, comprising:
a first pump;
a second pump;
a micromixer;
an agitating microchannel reactor;
a gas-liquid separator; and
a back pressure valve;
wherein the first pump is configured to feed an acetamidine hydrochloride solution; the second pump is configured to feed a (dimethylaminomethylene)malononitrile solution; a first inlet of the micromixer is connected to the first pump; a second inlet of the micromixer is connected to the second pump; an outlet of the micromixer is connected to an inlet of the agitating microchannel reactor; a top of the gas-liquid separator is provided with a first port, a second port and a third port; the first port is connected to an outlet of the agitating microchannel reactor; the second port is configured to introduce nitrogen to provide a pressure in the gas-liquid separator, where a pressure of the nitrogen is 0-2.5 MPa; the third port is connected to the back pressure valve; a back pressure of the back pressure valve is 0-2 MPa; and the pressure of the nitrogen is 0-0.5 MPa larger than a back pressure set by the back pressure valve;
the acetamidine hydrochloride solution and the (dimethylaminomethylene)malononitrile solution are pumped into the micromixer at the same time through the first pump and the second pump, respectively; the reaction mixture flowing out of the micromixer enters the agitating microchannel reactor and undergoes a continuous condensation-cyclization reaction; the reaction mixture flowing out of the agitating microchannel reactor enters the gas-liquid separator; a gas in the gas-liquid separator is discharged through the third port and the back pressure valve; and the reaction mixture is discharged from an outlet at a bottom of the gas-liquid separator, collected and subjected to separation and purification to obtain a target product 2-methyl-4-amino-5-cyanopyrimidine;

wherein the 2-methyl-4-amino-5-cyanopyrimidine is shown in formula (I):

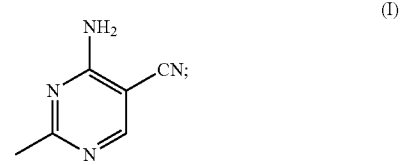

the acetamidine hydrochloride is shown in formula (II):

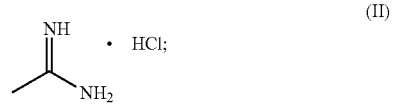

and
the (dimethylaminomethylene)malononitrile is shown in formula (III):

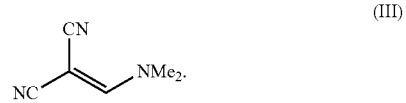

In some embodiments, the agitating microchannel reactor is a Coflore agitated cell reactor (AM Technology Co., Ltd, UK).

Compared to the traditional methods using a batch reactor, the method provided herein for preparing 2-methyl-4-amino-5-cyanopyrimidine using a micro reaction system including a micromixer and an agitating microchannel reactor has the following beneficial effects.

1. The agitating microchannel reactor has excellent mass and heat transfer and mixing performances, and can efficiently process a reaction system involving solid reactants or products, which largely shortens a reaction time of the continuous condensation-cyclization from more than 10 h (in a batch reactor) to less than 60 min. In addition, side reactions are largely suppressed, and a yield of the product 2-methyl-4-amino-5-cyanopyrimidine is increased from about 60% to 90% or more.

2. The method provided herein can be used to continuously prepare the target product from a starting material without any external interventions, and has high degree of automation and desirable time and space efficiency, significantly reducing the labor intensity and production cost.

3. The continuous condensation-cyclization reaction is completed in the reaction fluid channel of the agitating microchannel reactor and the mixing chambers, which has a relatively small total volume, so the method of the disclosure has a small online liquid holdup and an intrinsically safe process.

4. The multiphase mixing, mass transfer and reaction process are completed in the micromixer and the agitating microchannel reactor in the absence of a stirring device, which greatly reduces the energy consumption.

Figure 1:
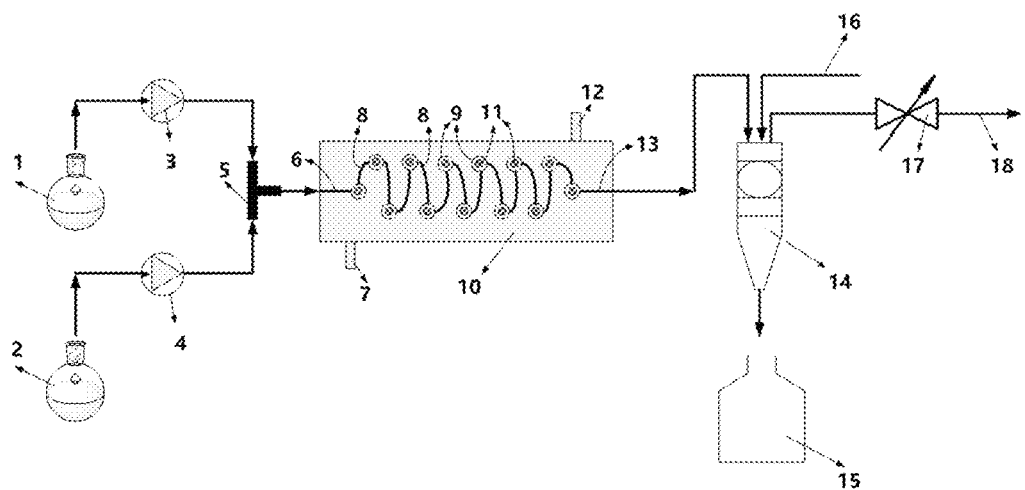
FIG. 1 is a schematic diagram of a structure of a micro reaction system in accordance with an embodiment of this disclosure.
Figure 2:
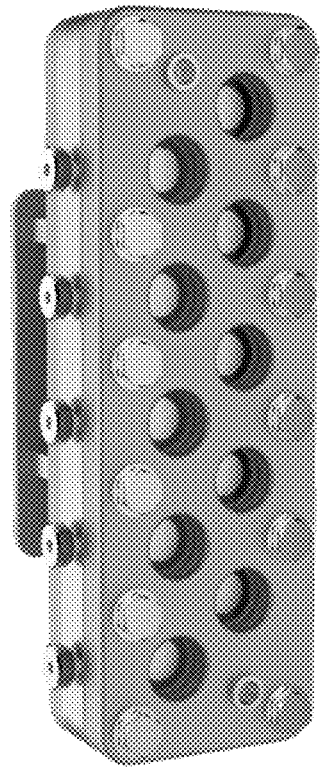
FIG. 2 is a perspective view of a Coflore agitated cell reactor (AM Technology Co., Ltd, UK) in accordance with in an embodiment of this disclosure.

In the drawings, 1, first container; 2, second container; 3, first pump; 4, second pump; 5, micromixer; 6. inlet channel; 7, temperature-control medium inlet; 8, reaction fluid channel; 9, mixing chamber; 10, agitating microchannel reactor; 11, stirrer; 12, temperature-control medium outlet; 13, outlet channel; 14, gas-liquid separator; 15, collection tank; 16, nitrogen pipeline; 17, back pressure valve; and 18, exhaust pipeline.

DETAILED DESCRIPTION OF EMBODIMENTS

The technical solutions of the present disclosure will be described in detail with reference to the accompanying drawings and embodiments. These embodiments are merely illustrative, and not intended to limit the scope of the present disclosure.

Unless otherwise specified, the experiments mentioned below are performed according to conventional methods and conditions, or according to the instructions of the manufacture. The reagents and raw materials used in the embodiments are all commercially available.

This disclosure provides a micro reaction system and a method for preparing 2-methyl-4-amino-5-cyanopyrimidine using the same, where the micro reaction system includes:

a first container 1 configured to store an acetamidine hydrochloride solution;

a second container 2 configured to store a (dimethylaminomethylene)malononitrile solution;

a first pump 3 configured to feed the acetamidine hydrochloride solution;

a second pump 4 configured to feed the (dimethylaminomethylene)malononitrile solution;

a micromixer 5;

an agitating microchannel reactor 10;

a gas-liquid separator 14;

a collection tank 15;

a nitrogen pipeline 16;

a back pressure valve 17;

an exhaust pipeline 18;

a plurality of connection pipelines;

a plurality of valves; and a temperature controller.

The micro reaction system is schematically shown in FIG. 1. A first inlet of the micromixer 5 is connected to the first pump 3 of the acetamidine hydrochloride solution, and a second inlet of the micromixer 5 is connected to the second pump 4.

An outlet of the micromixer 5 is connected to an inlet of the agitating microchannel reactor 10. A top of the gas-liquid separator 14 is provided with a first port, a second port and a third port. The first port is connected to an outlet of the agitating microchannel reactor 10. The second port is connected to the nitrogen pipeline 16. The third port is connected to the back pressure valve 17. An outlet of the back pressure valve 17 is connected to the exhaust pipeline 18. A temperature control medium outlet of the temperature controller is connected to a temperature control medium inlet 7 of the agitating microchannel reactor 10, and a temperature control medium outlet 12 of the agitating microchannel reactor 10 is connected to a temperature control medium inlet of the temperature controller.

The preparation of 2-methyl-4-amino-5-cyanopyrimidine using the above micro reaction system is described as follows.

(A) Acetamidine hydrochloride is dissolved in a methanol solution containing sodium methoxide at −20-15° C. to prepare an acetamidine hydrochloride solution, and (dimethylaminomethylene)malononitrile is dissolved in methanol to obtain a (dimethylaminomethylene)malononitrile solution.

(B) The acetamidine hydrochloride solution and the (dimethylaminomethylene)malononitrile solution are separately pumped into the micromixer 5 at the same time. The reaction mixture flowing out of the micromixer 5 enters the agitating microchannel reactor 10 and undergoes a continuous condensation-cyclization reaction. Then the reaction mixture flows out of the agitating microchannel reactor 10 and enters the gas-liquid separator 14. The gas is discharged through the third port and the back pressure valve 17, and the reaction mixture is discharged from an outlet at a bottom of the gas-liquid separator 14, collected and subjected to separation and purification to obtain a target product 2-methyl-4-amino-5-cyanopyrimidine.

The disclosure will be described in detail with reference to the embodiments. It should be noted that the agitating microchannel reactor used herein is a Coflore agitated cell reactor purchased from AM Technology Co., Ltd (UK), in which the reaction plate is provided with 1-10 mixing chambers communicated with each other through a reaction fluid channel. Each mixing chamber is provided with a stirrer therein. Reference can be made to related instructions for other detailed parameters.

Example 1

A methanol solution (200 mL) containing sodium methoxide (26.5 g, 0.49 mol) was cooled to 0° C., batchwise added with acetamidine hydrochloride (46.3 g, 0.49 mol in total) and stirred at 0° C. for 20 min. The reaction mixture was filtered, and a filtrate was collected and transferred to a conical flask. Then the filtrate and 350 mL of a solution of (dimethylaminomethylene)malononitrile (53 g, 0.44 mol) in methanol were simultaneously pumped into a T-type micromixer at a flow rate of 1.12 mL/min and 2.01 mL/min, respectively, such that a molar ratio of the acetamidine hydrochloride to the (dimethylaminomethylene)malononitrile was 1:0.92. A temperature in the T-type micromixer was controlled at 55° C. After mixed by the T-type micromixer, the reaction mixture subsequently entered a Coflore agitated cell reactor (AM Technology Co., Ltd, UK). The reactor had a reaction volume of 94 mL, and was vibrated at a frequency of 5 Hz. A temperature in the reactor was controlled at 55° C. A back pressure of a back pressure valve was adjusted to 0.1 MPa, and a pressure of the nitrogen introduced into a gas-liquid separator was 0.4 MPa. After reacted for 30 min, the reaction mixture was discharged through an outlet at a bottom of the gas-liquid separator, collected and filtered. A filter residue was collected, washed and dried to obtain a white solid, where a conversion rate of the (dimethylaminomethylene)malononitrile was greater than 99%, and a yield of 2-methyl-4-amino-5-cyanopyrimidine was 90.5%.

Example 2

The preparation of 2-methyl-4-amino-5-cyanopyrimidine in this example was basically the same as that in Example 1 except that a temperature in the T-type micromixer was controlled at 35° C. herein. In this example, a conversion rate of the (dimethylaminomethylene)malononitrile was 99%, and a yield of 2-methyl-4-amino-5-cyanopyrimidine was 90.4%.

Example 3

The preparation of 2-methyl-4-amino-5-cyanopyrimidine in this example was basically the same as that in Example 1 except that a temperature in the T-type micromixer was controlled at 65° C. herein. In this example, a conversion rate of the (dimethylaminomethylene)malononitrile was more than 99%, and a yield of 2-methyl-4-amino-5-cyanopyrimidine was 90.2%.

Example 4

The preparation of 2-methyl-4-amino-5-cyanopyrimidine in this example was basically the same as that in Example 1 except that a temperature in the T-type micromixer was controlled at 75° C. herein. In this example, a conversion rate of the (dimethylaminomethylene)malononitrile was more than 99%, and a yield of 2-methyl-4-amino-5-cyanopyrimidine was 90%.

Example 5

The preparation of 2-methyl-4-amino-5-cyanopyrimidine in this example was basically the same as that in Example 1 except that a temperature in the agitating microchannel reactor was controlled at 35° C. herein. In this example, a conversion rate of the (dimethylaminomethylene)malononitrile was 88%, and a yield of 2-methyl-4-amino-5-cyanopyrimidine was 81%.

Example 6

The preparation of 2-methyl-4-amino-5-cyanopyrimidine in this example was basically the same as that in Example 1 except that a temperature in the agitating microchannel reactor was controlled at 65° C. herein. In this example, a conversion rate of the (dimethylaminomethylene)malononitrile was more than 99%, and a yield of 2-methyl-4-amino-5-cyanopyrimidine was 90.8%.

Example 7

The preparation of 2-methyl-4-amino-5-cyanopyrimidine in this example was basically the same as that in Example 1 except that a temperature in the agitating microchannel reactor was at 75° C. herein. In this example, a conversion rate of the (dimethylaminomethylene)malononitrile was more than 99%, and a yield of 2-methyl-4-amino-5-cyanopyrimidine was 90.1%.

Example 8

The preparation of 2-methyl-4-amino-5-cyanopyrimidine in this example was basically the same as that in Example 1 except that a vibration frequency of the agitating microchannel reactor was at 6 Hz herein. In this example, a conversion rate of the (dimethylaminomethylene)malononitrile was more than 99%, and a yield of 2-methyl-4-amino-5-cyanopyrimidine was 92%.

Example 9

The preparation of 2-methyl-4-amino-5-cyanopyrimidine in this example was basically the same as that in Example 1 except that a vibration frequency of the reactor was at 7 Hz herein. In this example, a conversion rate of the (dimethylaminomethylene)malononitrile was more than 99%, and a yield of 2-methyl-4-amino-5-cyanopyrimidine was 93.6%.

Example 10

A methanol solution (200 mL) containing sodium methoxide (26.5 g, 0.49 mol) was cooled to 0° C., batchwise added with acetamidine hydrochloride (46.3 g, 0.49 mol in total) and stirred at 0° C. for 20 min. The reaction mixture was filtered, and a filtrate was collected and transferred to a conical flask. Then the filtrate and 350 mL of a solution of (dimethylaminomethylene)malononitrile (53 g, 0.44 mol) in methanol were simultaneously pumped into a T-type micromixer at a flow rate of 1.05 mL/min and 2.08 mL/min, respectively, such that a molar ratio of the acetamidine hydrochloride to the (dimethylaminomethylene)malononitrile was 1:1.02. A temperature in the T-type micromixer was controlled at 55° C. After mixed by the T-type micromixer, the reaction mixture subsequently entered a Coflore agitated cell reactor (AM Technology Co., Ltd, UK). The reactor had a reaction volume of 94 mL, and was vibrated at a frequency of 5 Hz. A temperature in the reactor was controlled at 55° C. A back pressure value of a back pressure valve was adjusted to 0.1 MPa, and a pressure of the nitrogen introduced into a gas-liquid separator was 0.4 MPa. After reacted for 30 mi, the reaction mixture was discharged through an outlet at a bottom of the gas-liquid separator, collected and filtered. A filter residue was collected, washed and dried to obtain a white solid, where a conversion rate of the (dimethylaminomethylene)malononitrile was 98%, and a yield of 2-methyl-4-amino-5-cyanopyrimidine was 90.1%.

Example 11

A methanol solution (200 mL) containing sodium methoxide (26.5 g, 0.49 mol) was cooled to 0° C., batchwise added with acetamidine hydrochloride (46.3 g, 0.49 mol in total) and stirred at 0° C. for 20 min. The reaction mixture was filtered, and a filtrate was collected and transferred to a conical flask. Then the filtrate and 350 mL of a solution of (dimethylaminomethylene)malononitrile (53 g, 0.44 mol) in methanol were simultaneously pumped into a Y-type micromixer at a flow rate of 1.21 mL/min and 1.93 mL/min, respectively, such that a molar ratio of the acetamidine hydrochloride to the (dimethylaminomethylene)malononitrile was 1:0.82. A temperature in the T-type micromixer was controlled at 55° C. After mixed by the T-type micromixer, the reaction mixture subsequently entered a Coflore agitated cell reactor (AM Technology Co., Ltd, UK). The reactor had a reaction volume of 94 mL, and was vibrated at a frequency of 6 Hz. A temperature in the reactor was controlled at 55° C. A back pressure value of a back pressure valve was adjusted to 0.1 MPa, and a pressure of the nitrogen introduced into a gas-liquid separator was 0.4 MPa. After reacted for 30 min, the reaction mixture was discharged through an outlet at a bottom of the gas-liquid separator, collected and filtered. A filter residue was collected, washed and dried to obtain a white solid, where a conversion rate of the (dimethylaminomethylene)malononitrile was greater than 99%, and a yield of 2-methyl-4-amino-5-cyanopyrimidine was 93%.

Example 12

The preparation of 2-methyl-4-amino-5-cyanopyrimidine in this example was basically the same as Example 1 except that a back pressure value of the back pressure valve was adjusted to 0 MPa herein. In this example, a conversion rate of the (dimethylaminomethylene)malononitrile was greater than 99%, and a yield of 2-methyl-4-amino-5-cyanopyrimidine was 89.6%.

Example 13

The preparation of 2-methyl-4-amino-5-cyanopyrimidine in this example was basically the same as Example 1 except that a back pressure value of the back pressure valve was adjusted to 1.0 MPa, and a pressure of nitrogen introduced by the gas-liquid separator was 1.3 MPa herein. In this example, a conversion rate of the (dimethylaminomethylene)malononitrile was greater than 99%, and a yield of 2-methyl-4-amino-5-cyanopyrimidine was 91.5%.

Example 14

A methanol solution (200 mL) containing sodium methoxide (26.5 g, 0.49 mol) was cooled to 0° C., batchwise added with acetamidine hydrochloride (46.3 g, 0.49 mol in total) and stirred at 0° C. for 20 min. The reaction mixture was filtered, and a filtrate was collected and transferred to a conical flask. Then the filtrate and 350 mL of a solution of (dimethylaminomethylene)malononitrile (53 g, 0.44 mol) in methanol were simultaneously pumped into a T-type micromixer at a flow rate of 1.68 mL/min and 3.01 mL/min, respectively, such that a molar ratio of the acetamidine hydrochloride to the (dimethylaminomethylene)malononitrile was 1:0.92. A temperature in the T-type micromixer was controlled at 55° C. After mixed by the T-type micromixer, the reaction mixture subsequently entered a Coflore agitated cell reactor (AM Technology Co., Ltd, UK). The reactor had a reaction volume of 94 mL, and was vibrated at a frequency of 5 Hz. A temperature in the reactor was controlled at 55° C. A back pressure value of a back pressure valve was adjusted to 0.1 MPa, and a pressure of the nitrogen introduced into a gas-liquid separator was 0.4 MPa. After reacted for 20 mi, the reaction mixture was discharged through an outlet at a bottom of the gas-liquid separator, collected and filtered. A filter residue was collected, washed and dried to obtain a white solid, where a conversion rate of the (dimethylaminomethylene)malononitrile was greater than 99%, and a yield of 2-methyl-4-amino-5-cyanopyrimidine was 90%.

Comparative Example 1

Provided herein was a method for preparing 2-methyl-4-amino-5-cyanopyrimidine using a batch reactor, where the batch reactor was a 150 mL round-bottom flask.

Specifically, 33.6 mL of a solution of sodium methoxide (4.46 g, 0.083 mol) in methanol was cooled to 0° C., batchwise added with acetamidine hydrochloride (7.79 g, 0.082 mol in total), and stirred at −10° C. for 60 min. The reaction mixture was filtered, and a filtrate was collected and transferred to a round-bottom flask pre-filled with 60.4 mL of a solution of (dimethylaminomethylene)malononitrile (9.14 g, 0.076 mol) in methanol. Then the reaction mixture was reacted at 0° C. under stirring, where the reaction mixture was sampled and analyzed regularly. The analysis results demonstrated that the substrate (dimethylaminomethylene) malononitrile had a conversion rate of about 48% after reacted for 3 h; about 67% after reacted for 6 h; about 82% after reacted for 9 h; and about 97% after reacted for 12 h; and after the reaction was performed for 12 h, a yield of 2-methyl-4-amino-5-cyanopyrimidine was 60%.

The Comparative Example 1 was the same as Example 1 in the feed ratio of reaction materials. Compared to the batch reactor, the micro reaction system provided herein greatly shortened the reaction time and improved the yield of the target product 2-methyl-4-amino-5-cyanopyrimidine by 30% or more. In addition, with the help of the micro reaction system, the preparation process can be performed continuously with simple operation and high degree of automation, allowing for a largely improved efficiency.

What is claimed is:
1. A method for preparing 2-methyl-4-amino-5-cyanopyrimidine using a micro reaction system, the micro reaction system comprising a micromixer and an agitating microchannel reactor communicated in sequence, and the method comprising:
  (1) pumping an acetamidine hydrochloride solution and a (dimethylaminomethylene)malononitrile solution separately into the micromixer at the same time followed by mixing;
  (2) allowing the reaction mixture flowing out of the micromixer to enter the agitating microchannel reactor; and subjecting the reaction mixture to condensation-cyclization reaction; and
  (3) collecting the reaction mixture flowing out of the micro reaction system; and subjecting the reaction mixture to separation and purification to obtain a target product 2-methyl-4-amino-5-cyanopyrimidine;
wherein the 2-methyl-4-amino-5-cyanopyrimidine is shown in formula (I); the acetamidine hydrochloride is shown in formula (II); the (dimethylaminomethylene) malononitrile is shown in formula (III); the condensation-cyclization reaction is shown in the following reaction scheme;

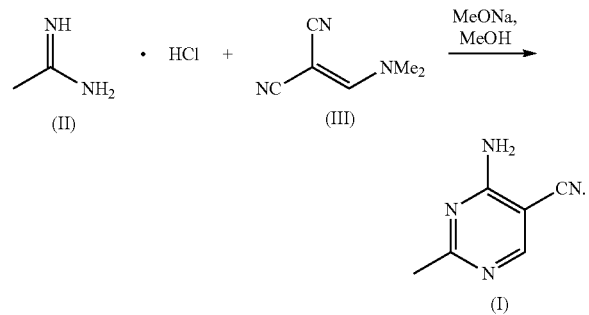

2. The method of claim 1, wherein in step (1), the acetamidine hydrochloride solution is prepared by dissolving acetamidine hydrochloride in a methanol solution containing sodium methoxide at −20-15° C.; a molar concentration of sodium methoxide in the methanol solution is 0.5-7 mol/L; and a molar ratio of acetamidine hydrochloride in the acetamidine hydrochloride solution to the sodium methoxide in the acetamidine hydrochloride solution is controlled at 1:0.7-1.3.

3. The method of claim 1, wherein in step (1), the (dimethylaminomethylene)malononitrile solution is prepared by dissolving (dimethylaminomethylene)malononitrile in methanol; and a molar concentration of the (dimethylaminomethylene)malononitrile in the (dimethylaminomethylene)malononitrile solution is 0.8-1.8 mol/L.

4. The method of claim 1, wherein in step (1), the micromixer is a static mixer, a T-shaped micromixer, a Y-shaped micromixer, a coaxial flow micromixer or a flow-focusing micromixer.

5. The method of claim 1, wherein in step (1), flow rates of the acetamidine hydrochloride solution and the (dimethylaminomethylene)malononitrile solution pumped into the micromixer are controlled to adjust a molar ratio of the acetamidine hydrochloride to the (dimethylaminomethylene)malononitrile to 1:0.6-1.2; and a temperature in the micromixer is controlled at −10-100° C.

6. The method of claim 1, wherein the micro reaction system further comprises:
a first pump for feeding the acetamidine hydrochloride solution;
a second pump for feeding the (dimethylaminomethylene)malononitrile solution;
a gas-liquid separator; and
a back pressure valve;
wherein a first inlet of the micromixer is connected to the first pump; a second inlet of the micromixer is connected to the second pump; an outlet of the micromixer is connected to an inlet of the agitating microchannel reactor; a top of the gas-liquid separator is provided with a first port, a second port and a third port; the first port is connected to an outlet of the agitating microchannel reactor; the second port is configured to introduce nitrogen to provide a pressure in the gas-liquid separator, where a pressure of the nitrogen is 0-2.5 MPa; the third port is connected to the back pressure valve, where a back pressure of the back pressure valve is 0-2 MPa; and the pressure of the nitrogen is 0-0.5 MPa larger than a back pressure set by the back pressure valve.

7. The method of claim 1, wherein in step (2), the agitating microchannel reactor comprises:
at least one reaction plate; and
at least one heat exchange plate;
wherein the at least one heat exchange plate fastened to the at least one reaction plate; each of the at least one reaction plate is provided with at least one inlet channel, at least one outlet channel, N reaction fluid channel(s) and N+1 mixing chambers, wherein N is an integer equal to or greater than 1; each of the N+1 mixing chambers is a three-dimensional cavity; each of the N+1 mixing chambers is provided with a stirrer therein; the N+1 mixing chambers are communicated with the N reaction fluid channel(s); one end of the at least one inlet channel is connected to an inlet of the agitating microchannel reactor, and the other end of the at least one inlet channel is communicated with a mixing chamber adjacent thereto; one end of the at least one outlet channel is connected to an outlet of the agitating microchannel reactor, the other end of the at least one outlet channel is communicated with a mixing chamber adjacent thereto; each of the at least one heat exchange plate is provided with a temperature-control medium channel; two ends of the temperature-control medium channel are provided with a temperature-control medium inlet and a temperature-control medium outlet; the agitating microchannel reactor is arranged at a base or a support that is vibratile horizontally or vertically with a constant amplitude; a hydraulic diameter of the at least one inlet channel is 0.1-20 mm; a hydraulic diameter of the at least one outlet channel is 0.1-20 mm; a hydraulic diameter of the N reaction fluid channel(s) is 0.1-20 mm; a depth of each of the N+1 mixing chambers is 40-90% of a thickness of the at least one reaction plate; a hydraulic diameter of a cross-section of each of the N+1 mixing chambers is 2-50 mm; a volume of each of the N+1 mixing chambers is 1-50 mL; the stirrer is 30-95% by volume of each of the N+1 mixing chambers; and a vibration frequency of the base or support is controlled at 0-15 Hz.

8. The method of claim 7, wherein the N+1 mixing chambers are cylindrical or prismatic.

9. The method of claim 7, wherein the agitating microchannel reactor is a Coflore agitated cell reactor.

10. The method of claim 1, wherein in step (2), a temperature in the agitating microchannel reactor is controlled at 0-100° C., and a residence time of the reaction mixture in the agitating microchannel reactor is controlled to 1-60 min.

11. A micro reaction system for preparing 2-methyl-4-amino-5-cyanopyrimidine, comprising:
a first pump;
a second pump;
a micromixer;
an agitating microchannel reactor;
a gas-liquid separator; and
a back pressure valve;
wherein the first pump is configured to feed an acetamidine hydrochloride solution; the second pump is configured to feed a (dimethylaminomethylene)malononitrile solution; a first inlet of the micromixer is connected to the first pump; a second inlet of the micromixer is connected to the second pump; an outlet of the micromixer is connected to an inlet of the agitating microchannel reactor; a top of the gas-liquid separator is provided with a first port, a second port and a third port; the first port is connected to an outlet of the agitating microchannel reactor; the second port is configured to introduce nitrogen to provide a pressure in the gas-liquid separator, where a pressure of the nitrogen is 0-2.5 MPa; the third port is connected to the back pressure valve; a back pressure of the back pressure valve is 0-2 MPa; and the pressure of the nitrogen is 0-0.5 MPa larger than a backpressure set by the back pressure valve;
the acetamidine hydrochloride solution and the (dimethylaminomethylene)malononitrile solution are pumped into the micromixer at the same time through the first pump and the second pump, respectively; the reaction mixture flowing out of the micromixer enters the agitating microchannel reactor and undergoes a continuous condensation-cyclization reaction; the reaction mixture flowing out of the agitating microchannel reactor enters the gas-liquid separator; a gas in the gas-liquid separator is discharged through the third port and the back pressure valve; and the reaction mixture is discharged from an outlet at a bottom of the gas-liquid separator, collected and subjected to separation and purification to obtain a target product 2-methyl-4-amino-5-cyanopyrimidine;

wherein the 2-methyl-4-amino-5-cyanopyrimidine is shown in formula (I):

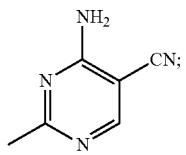

(I)

the acetamidine hydrochloride is shown in formula (II):

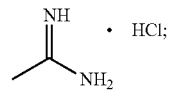

(II)

and the (dimethylaminomethylene)malononitrile is shown in formula (III):

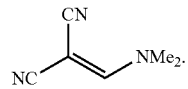

(III)

* * * * *